(12) United States Patent
Neugebauer et al.

(10) Patent No.: US 8,262,637 B2
(45) Date of Patent: Sep. 11, 2012

(54) FASTENING TAPE FOR A HYGIENE ITEM, DIAPER, METHOD OF CLOSING A DIAPER, TAPE MATERIAL AND WINDING OF A TAPE MATERIAL

(75) Inventors: Robert Neugebauer, Neunkirchen (DE); Wolfgang Silberling, Nürnberg (DE)

(73) Assignee: Koester GmbH & Co. KG, Altendorf (DE)

( * ) Notice: Subject to any disclaimer, the term of this patent is extended or adjusted under 35 U.S.C. 154(b) by 994 days.

(21) Appl. No.: 10/588,692

(22) PCT Filed: Feb. 8, 2005

(86) PCT No.: PCT/DE2005/000209
§ 371 (c)(1),
(2), (4) Date: Dec. 14, 2006

(87) PCT Pub. No.: WO2005/074852
PCT Pub. Date: Aug. 18, 2005

(65) Prior Publication Data
US 2007/0134489 A1    Jun. 14, 2007

(30) Foreign Application Priority Data

Feb. 8, 2004 (DE) .......... 10 2004 006 219
Feb. 8, 2004 (DE) .......... 10 2004 006 221

(51) Int. Cl.
*A61F 13/15* (2006.01)
*A61F 13/20* (2006.01)
(52) U.S. Cl. ........................ 604/389; 604/391

(58) Field of Classification Search .................. 604/386, 604/391, 389
See application file for complete search history.

(56) References Cited

U.S. PATENT DOCUMENTS

| | | |
|---|---|---|
| 4,237,890 A | 12/1980 | Laplanche |
| 4,670,012 A | 6/1987 | Johnson |
| 5,399,219 A | 3/1995 | Roessler et al. |
| 5,624,429 A | 4/1997 | Long et al. |
| 5,759,317 A | 6/1998 | Justmann |
| 5,997,522 A | 12/1999 | Provost et al. |
| 6,210,389 B1 | 4/2001 | Long et al. |
| 6,454,751 B1 | 9/2002 | Olson |
| 7,037,457 B2 | 5/2006 | Seidel et al. |
| 2002/0095130 A1 | 7/2002 | Seitter et al. |
| 2003/0004490 A1 | 1/2003 | Larsson et al. |
| 2003/0009144 A1* | 1/2003 | Tanzer et al. ................. 604/391 |
| 2003/0023322 A1 | 1/2003 | Laghi |
| 2003/0034583 A1 | 2/2003 | Provost |
| 2003/0060794 A1 | 3/2003 | Olson |

(Continued)

FOREIGN PATENT DOCUMENTS

DE    28 56 869    7/1979

(Continued)

OTHER PUBLICATIONS

International Search Report.

(Continued)

*Primary Examiner* — Melanie Hand
(74) *Attorney, Agent, or Firm* — Collard & Roe, P.C.

(57) ABSTRACT

A fastening tape for a hygiene item with a targeted design of a mechanical closing area and a closing area of the tape that is closable by means of an adhesive is extremely versatile and also allows very inexpensive production.

11 Claims, 8 Drawing Sheets

U.S. PATENT DOCUMENTS

Figure 1:
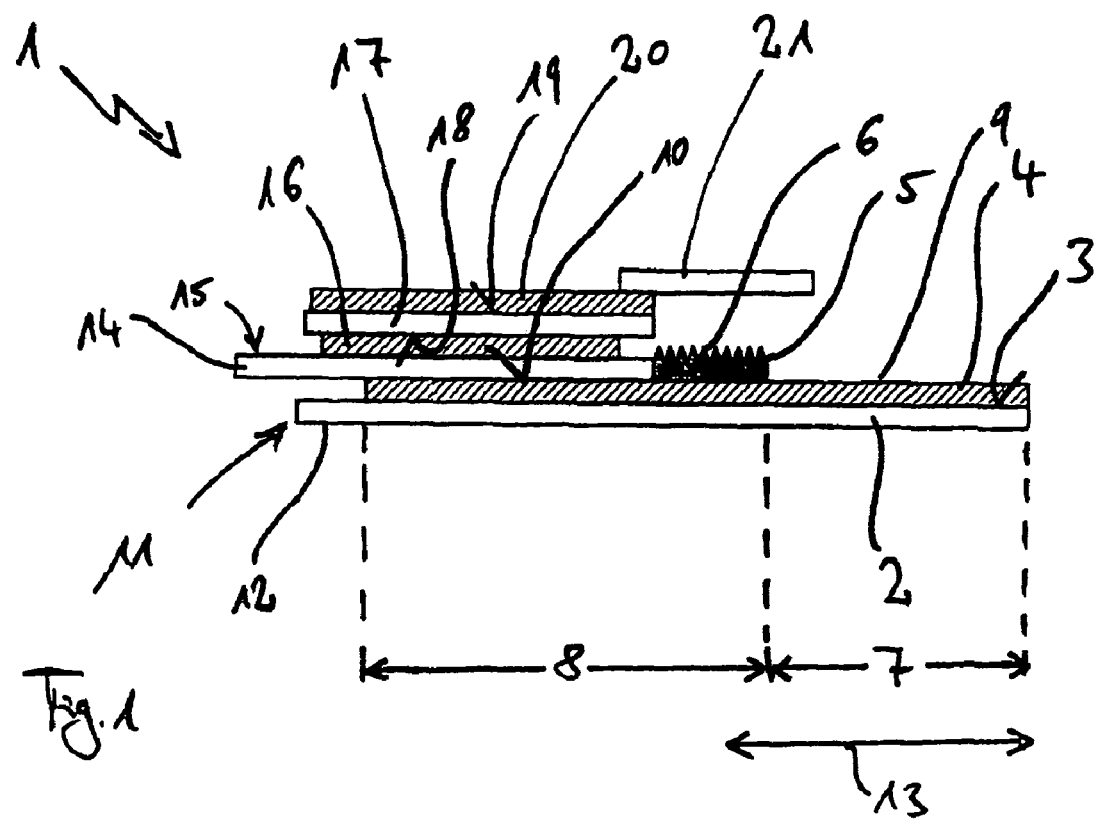

| | | | |
|---|---|---|---|
| 2003/0212416 A1 * | 11/2003 | Cinelli et al. | 606/134 |
| 2004/0194260 A1 | 10/2004 | Wendelstorf et al. | |
| 2004/0236301 A1 | 11/2004 | Wendelstorf et al. | |

FOREIGN PATENT DOCUMENTS

| | | |
|---|---|---|
| DE | 83 27 230 | 1/1984 |
| DE | 197 32 499 | 2/1999 |
| DE | 101 29 180 | 10/2002 |
| DE | 101 40 622 | 3/2003 |
| DE | 101 40 621 | 7/2003 |
| EP | 0 233 704 | 8/1987 |
| EP | 0321 232 | 6/1989 |
| EP | 0 235 014 | 7/1991 |
| EP | 0 233 704 | 7/1992 |
| EP | 0 755 665 | 1/1997 |
| EP | 0 793 953 | 9/1997 |
| EP | 0 795 307 | 9/1997 |
| EP | 0 840 585 | 5/1998 |
| EP | 0 941 730 | 9/1999 |
| EP | 0 983 760 | 3/2000 |
| EP | 1 000 598 | 5/2000 |
| EP | 0 800 378 | 11/2000 |
| EP | 0 820 264 | 5/2001 |
| EP | 1 024 774 | 1/2003 |
| FR | 2 586 558 | 6/1987 |
| FR | 2 606 257 | 5/1998 |
| GB | 2 296 423 | 7/1996 |
| JP | 62 142825 | 6/1987 |
| JP | 8-2365 | 1/1996 |
| WO | WO 96/31181 | 10/1996 |
| WO | WO 97/23186 | 7/1997 |
| WO | WO97/32555 | 9/1997 |
| WO | WO 97/36566 | 10/1997 |
| WO | WO 00/27236 | 5/2000 |
| WO | WO 00/27330 | 5/2000 |
| WO | WO 01/67911 | 9/2001 |
| WO | WO 01/68019 | 9/2001 |
| WO | WO 01/74283 | 10/2001 |
| WO | WO 02/49567 | 6/2002 |
| WO | WO 02/49568 | 6/2002 |
| WO | WO 03/003962 | 1/2003 |
| WO | WO 2005/000180 | 1/2005 |
| WO | WO 2005/000181 | 1/2005 |

OTHER PUBLICATIONS

D. Satas, "Handbook of Pressure Sensitive Adhesive Technology," $2^{nd}$ Edition, 1989, pp. 61, 77-79, 84-87 and 89-90.

* cited by examiner

FASTENING TAPE FOR A HYGIENE ITEM, DIAPER, METHOD OF CLOSING A DIAPER, TAPE MATERIAL AND WINDING OF A TAPE MATERIAL

CROSS REFERENCE TO RELATED APPLICATIONS

Applicants claim priority under 35 U.S.C. §119 of German Application No. 10 2004 006 219.6 filed Feb. 8, 2004 and German Application No. 10 2004 006 221.8 filed Feb 8, 2004. Applicants also claim priority under 35 U.S.C. §365 of PCT/DE2005/000209 filed Feb. 8, 2005. The international application under PCT article 21(2) was not published in English.

The invention relates to a fastening tape for a hygiene item, a diaper, a method for closing a diaper, a tape material and a winding of a tape material. More precisely, the invention relates to such fastening tapes and their context in which a closing area on the closing tape has a component of a mechanical two-component fastening system and an exposed adhesive layer for detachable closing of the hygiene item.

The diaper-fastening tapes are attached to the diaper at the time of its production, so that a user of the diaper can close the diaper with the help of the diaper-fastening tapes after applying it to the body. Frequently, two diaper-fastening tapes are secured for this purpose on the side diaper wings of the front side or back side of the diaper. This attachment is adjusted so that it will endure at least of the foreseeable lifetime of the diaper and is generally not detachable without destroying the diaper and/or the fastening tape.

Such fastening tapes are known from EP 0 321 232 B1, for example. The diaper-fastening tapes described there consist of a fastening carrier which has a fastening area for permanent fastening to the diaper and a closing area facing a free user end that protrudes away from the diaper, said closing area having a hook area with an exposed adhesive layer. The hook area and the exposed adhesive layer form a closing area in their entirety for detachable closing of the diaper. According to one variant presented there, the hook area may not only be arranged on the free end of the closing area but may also be provided with an exposed adhesive coating over a partial area centrally in the closing area, so that a partial area with exposed adhesive is formed on both sides of the hook area.

JP 8-2365 B also discloses a diaper having a diaper-fastening tape on whose closing area one or two central hook areas and adhesive strips surrounding them are provided.

FR 2 586 558 A1 discloses a diaper having a belt-shaped fastening tape. In the front section of the back sheet, small holding areas with hooks may optionally be provided. In this case, it is proposed that the diaper-fastening tapes shall optionally receive a loop material in their closing areas, while an adhesive surface facing the free user end is provided.

WO 00/27236 discloses diaper-fastening tapes having hook areas and exposed adhesive areas in the closing area in a wide variety of embodiments.

Other fastening tapes, usually for baby diapers or adult incontinency diapers are disclosed in, among other citations, U.S. Pat. No. 5,624,429, EP 0795307A2, EP 0793953A2, EP 0840585 B1, DE 10129180 A1, EP 0235014B1, EP 0233704A2, FR 2606257, U.S. Pat. Nos. 6,210,3 89 B1, 5,759,317, 5,399,219, EP 1000598A1, DE 197 32 499 A1, WO 02/49568 A1, WO 02/49567A1, WO 01/74283 A1, WO 00/27330 A1, EP 1 024 774 B1, U.S. Pat. No. 4,670,012, DE 101 40 622 A1, DE 2856869 A1, DE 10140621 A1, WO 97/32555 A1, WO 96/31181 A1, WO 97/23186 A1, U.S. Pat Nos. 5,759,317, 5,399,219, 6,210,389 B1, 5,624,429, EP 0 233 704 B1, EP 0 800 378 B1, U.S. Pat. Nos. 6,454,751 B1, 5,997,522, US 2003/0009144 A1, US 2003/0023322, US 2003/0034583 A1, WO 01/67911 A2 and WO 01/68019 A1.

The main object of the diaper-fastening tapes is to keep the diapers securely closed and, in doing so, to induce the least possible sacrifice in terms of wearing comfort. In the case of both infant diapers and adult diapers, a wide variety of forces may act on the closing system of the diaper.

The object of the present invention is to propose diapers, diaper-fastening tapes and tape material for the production thereof which are improved with respect to their closing system and/or have an improved price/performance ratio.

According to one aspect of the present invention, this object is achieved by a fastening tape for a hygiene item, in particular for a baby diaper or an incontinency diaper, having a fastening area for permanent fastening on the hygiene item and having a closing area for simultaneous detachable connecting to a surface of the hygiene item, whereby the closing area has two surface areas which have components of different closing systems which is characterized in that the one surface area has a shear-off securing means and the other surface area has a pop-off securing means.

In this regard, the following should be explained: fastening tapes of the definitive type here have a fastening area and a closing area. The fastening area usually has an exposed adhesive surface or the like by means of which it can be permanently attached by adhesive to a diaper, for example. The part of the tape which is not permanently glued and/or joined to the diaper is then to be referred to as the free user end of the fastening tape. The user end of the fastening tape serves to allow the user to grip the tape for closing the diaper after applying it to the body or after folding it together after removing it from the body and can lead to a landing zone provided for this purpose on a front section of the back sheet of the diaper. Toward the user end, the fastening tape has a closing area which may have, for example, a mechanical closing component, in particular a hook area, and an adhesive area, in which case then the shear-off securing means may be formed by the mechanical closing component and the pop-off securing means may be formed by the adhesive area. The user pressing this double function closing area against the landing zone to close and seal the diaper. This leads to a closure of the mechanical two-component closing system, while at the same time the exposed adhesive area of the closing area is detachably glued to the landing zone.

Such a generic type of diaper-fastening tape may be derived from EP 0 321 232 B1 and JP 8-2365 B, for example. The mechanical closing component here interacts with a frontal tape which is arranged on the front section of the back sheet of the diaper and carries the complementary component of the mechanical closing system. The adhesive layer interacts with corresponding film areas on the back sheet which are offered for applying the fastening tape when the diaper is folded up for disposal—or it interacts with film areas on a release tape which is arranged in such a way that it is presented for detachable fastening of the closing area during fabrication of the diaper. To this extent according to the state of the art, a distribution of tasks according to which the fastening tape is to be kept closed via the mechanical closing component during the time while the diaper is being worn, whereas in production and disposal, this task is accomplished by the connection between the adhesive layer of the closing area and a receiving film provided for this purpose.

Against this background, the present invention recognizes that a closing area having two different securing means each being specialized in its functions, namely a pop-off securing means, such as an adhesive layer, and a shear-off securing means such as a mechanical component, can be utilized in an excellent manner for keeping the diaper closed with these combined forces and can be utilized in the production as well while being worn and for disposal.

Accordingly, according to the present invention, the shear-off securing means, i.e., the component of a first closing system arranged in the first surface area, must counteract forces acting perpendicularly on the tape to a greater extent than is the case due to the component of the second fastening system arranged in the second surface area. Conversely, according to this invention the pop-off securing means, i.e., the component of the second fastening system arranged in the second surface area must withstand any forces acting on the tape in parallel and to a greater extent than is the case due to the component of the first fastening system arranged in the first surface area. These force relationships are especially preferably also to be found in the forces per unit of area, although that need not necessarily be the case.

The pop-off securing means ensures to a great extent that the fastening tape cannot spring away, i.e., pop off or be pulled away from a landing zone in a direction perpendicular to the tape surface. The pop-off securing means is thus preferably an adhesive layer which can interact with a textile material, in particular the back sheet.

The shear-off securing means serves to a great extent to prevent the fastening tape from sliding over the landing zone. It thus prevents a shear-off effect from occurring between the fastening tape and the landing zone in the plane in the fastening tape. It absorbs the shearing forces between the landing zone and the fastening tape in particular. For example, a mechanical hook-and-loop fastening system is very suitable here.

It is self-evident that the distribution of the main points of the function between the pop-off securing means and the shear-off securing means described above is not exclusive. In particular, the mechanical fastening system will also make a contribution toward maintaining the fastening normal to the plane of the fastening tape. Likewise, the adhesive bond will assume some of the shearing forces. However, it has been found that in the interaction of the mechanical connection and the adhesive connection, the mechanical fastening system counteract shearing forces in particular while the adhesive prevents vertical lifting of the tape away from the textile material so that the mechanical fastening can continue to remain in effect.

According to a preferred aspect of this invention, between the shear-off securing means and the free end of the fastening tape, the remaining closing area covers a larger surface area than does the shear-off fastening means.

Consequently, this aspect of the invention must ensure an adequate force for securely keeping the diaper closed with the help of two types of fastening. Under the aspect of the improved cost-benefit ratio and the quality of the fastening which are presented as the task here, the aspect proposed here for the present invention therefore suggests this design: starting at the free user end, the closing area should begin with a pop-off securing means. At the same level as the fastening tape (then over only a portion of the tape width accordingly) a shear-off securing means may already be present. The definitive factor, however, is that at least a portion of the bordering edge of the closing area tracing the free user end must have a pop-off securing means.

In view of the distribution of tasks according to the main focus, it is advantageous that the pop-off securing means is provided first on the free user end. Shearing forces between the tape and the landing zone should already be absorbed in the part of the closing area that is closer to the fastening area. Thus, little or no shearing forces should prevail on the end of the closing area pointing toward the free user end. To this extent, the required task at this end thus at least largely consists of preventing the fastening tape from unintentionally falling down perpendicular to the plane of the tape.

With such a constellation it is thus proposed according to the aspect described above that the remaining closing area between the shear-off securing means and the free end shall be greater than the shear-off securing means. This carries the idea of distribution of tasks to its logical end and employs it inexpensively. To cover an area with a mechanical fastening component, e.g., with hooks, is definitely more complex and more cost-intensive than providing the same area with an adhesive layer. The present invention has recognized that even a very small hook area in the closing area is sufficient to absorb the usual shearing forces that occur in wearing and disposing of a diaper. The hook area may thus be kept quite small and in particular may be less than half the total area of the closing area. In this way, an enlarged area can be used for the pop-off securing means—which can usually be implemented in a quite inexpensive manner. In particular, the area of the pop-off securing means may even be larger than the area of the shear-off securing means. The large adhesive area according to the proposed aspect of the present invention thus corresponds to the relatively small area of the mechanical fastening component in the closing area of the fastening tape.

At the same time, the proposed arrangement makes it possible for the mechanical fastening system not to have to be designed to be so efficient. In particular, when the remaining closing area between the shear-off securing means and the free end is not too much larger than the shear-off securing means, e.g., with a hook-and-loop fastening system the textile material that provides the loops may be selected to be a velour quality. To this extent lower requirements may be made of the textile structure of a frontal tape, for example, which embodies the landing zone for the fastening tape and which must have a large mesh according to the state of the art. For example even simple nonwoven materials may be used here.

This makes it possible in particular to completely eliminate the frontal tape under some circumstances. In this case, the diaper-fastening tape according to this aspect of the invention is pressed directly against the nonwoven on the back sheet of the diaper. The frontal tape may be omitted. This allows a considerable reduction in the total cost of a diaper.

In the present context, the term "hook-and-loop fastening system" and/or mechanical fastening system refers to a fastening system in which an arrangement of a first male component protruding out of a surface is able to engage behind recesses, loops, openings, fibers or the like of a second female component, thus producing a resistance against shearing and/or separation. This is different from adhesive fastening systems in which a corresponding connection of two modules is ensured by adhesion, e.g., through the use of an adhesive.

For the precise arrangement of pop-off securing means and shear-off securing means in the closing area it is proposed that the shear-off securing means shall tend to be shifted toward the fastening area of the fastening tape. A pop-off securing means on the side of the shear-off securing means pointing toward the fastening area is definitely less effective in comparison with an arrangement of the same area as proposed here. To this extent it is even proposed that the pop-off securing means on the side toward the free user end of the total shear-off securing means shall be larger than the area of this total shear-off securing means.

It is self-evident that as the adhesive a pressure-sensitive adhesive should be used or can be used at least in the closing area.

Since it is possible according to the aspect of the present invention as already proposed to eliminate the frontal tape, another aspect of the present invention proposes a method for closing a diaper for applying it to the body and/or for disposing of the diaper whereby to close the diaper a connection is established between a closing area of a diaper-fastening tape on a diaper wing and a landing zone, especially on a front section, whereby the method is characterized in that a surface area of a textile back sheet of the diaper is selected directly as the landing zone.

By analogy with this idea, a third aspect of the present invention proposed a coordination between the closing area and a textile back sheet such that the diaper-fastening tape is detachably connectable to a landing zone on the textile back sheet via the closing area. It is obvious that a frontal tape with such a setting of the combined holding force of the closing area on the back sheet is superfluous. Furthermore, when the frontal tape is omitted, this yields the possibility of using an enormous landing zone because practically the entire front section of the back sheet can be used for this purpose. This is especially advantageous when applying the diaper to the body for wearing but also especially in disposal of the diaper. In particular, the diaper-fastening tapes need no longer have such great elasticity as required in the past because a much larger landing zone is made available.

In a preferred embodiment, the back sheet has and/or is formed from a nonwoven material on its outside. A nonwoven material has the disadvantage with respect to a mechanical fastening system that a hook material and/or the part of a mechanical fastening system that engages behind the mating part will find it relatively difficult to engage here. To this extent, a woven or knit material which is preferred according to the state of the art is more expensive but can provide deeper and more accessible loops. As the landing surface for an adhesive, a nonwoven material, like any other textile material, is also not optimal. Smooth surfaces such as the films known from the state of the art as back sheets for diapers are inherently more suitable. Through the present invention however these disadvantages can be converted into advantages. For example, an adhesive adheres better to a nonwoven material than a woven and/or knit material which has sufficiently deep loops for a mechanical fastening system. On the other hand, hooks or similar protrusions may protrude into the nonwoven material and may provide a shear-off securing means, which is impossible in interaction with a film. To this extent, due to the functional separation between the shear-off securing means and the pop-off securing means, a fastener system having a nonwoven back sheet is made available, having sufficient closing force and, since a nonwoven material is relatively inexpensive in comparison with a knit or woven material, this eliminates the need for a separate frontal tape, so the entire outside of the diaper can participate in the haptic feedback.

As an alternative and/or cumulatively, the closing area as seen from the fastening area may have at least in part the shear-off securing means, preferably in the form of a hook. This is also a logical application of the inventive finding regarding how functions and forces can be distributed between the two systems for closing the diaper as provided in the closing area. It has already been mentioned that the closing area may advantageously have a shear-off securing means toward the fastening area. In particular the hooks of a hook-and-loop fastening system are recommended for this purpose. If hooks are provided on the edge of the closing area over at least a portion of the width of the tape, facing the fastening area, then there is an especially good targeted transfer forces between the front section and the back section of the diaper—very little force need be absorbed within the plane of the fastening tape to the side of the shear-off securing means. The pop-off securing with adhesive is not primarily intended for this purpose. To this extent, there is no adhesive area because it is inappropriately provided. This also helps to save on costs and to provide a particularly reliable closure.

Ideally, the shear-off securing means should first be provided in the closing area as seen from the fastening area whereas the pop-off securing means is provided first in the closing area as seen from the user end.

The fastening tape preferably includes a separable target tape which is disposed on the closing area and partially covers it, leaving exposed at least a part of the shear-off securing means, however.

If the target tape has adhesive on its rear side, i.e., on the side facing away from the fastening tape, it can be attached there to the front section, more precisely in the landing zone, especially in the landing zone where the closing area of the diaper-fastening tape will land when the diaper is closed up. In this case only the diaper-fastening tape need be gripped jointly together with the target tape coated with adhesive on its rear side, then the diaper is brought into its ready-to-use state and/or its disposal state and the diaper-fastening tape is pressed against the landing zone. At the same time with the released hooks of the closing area, in this case the adhesive coating rear side of the target tape comes in contact with the landing zone of the back sheet. The target tape is instantaneously undetachably bonded to the back sheet and thus becomes the frontal tape in the landing zone on the back sheet there. When the diaper-fastening tape is pulled away from the front section, the target tape, now attached securely, remains on the front section. The original diaper-fastening tape with the target tape arranged in the closing area becomes detached so that after pulling the fastening tape away from the target tape the user is holding in his/her hand only the traditional diaper-fastening tape with a mechanical component and an adhesive surface.

When the diaper is to be closed again after pulling the tape away in this fashion, the exposed adhesive surface of the closing area again comes in contact with the target tape in the landing zone while the hooks of the closing area come to lie at least in part again next to the target tape (now serving as the frontal tape) on the back sheet of the diaper in the landing zone. Thus, this again results in the advantageous double-fastening style.

If the diaper is disposed of after use, then it is likely, depending on the folding technique, that the diaper-fastening tape will come to lie at another location on the back sheet of the diaper than it would have assumed when wearing the diaper. At this point in time, however, there is also the double fastening effect of the closing area: the hooks of the mechanical fastening system become hooked directly to the surface of the back sheet. At the same time, the exposed adhesive layer of the closing area holds down the diaper-fastening tape on the surface of the back sheet. Due to this holding down effect, it is not absolutely necessary for the hooks to penetrate very deeply into the textile material and engage behind individually fibers or mesh, for example, because the adhesive reliably prevents them from being separated again.

Such an arrangement makes is possible in particular to select the adhesive with which the target tape is to be secured on the back sheet in such a way that it adheres extremely securely to it. This may go to such an extent that the target tape can no longer be nondestructively removed from the back sheet. The latter is not absolutely necessary because the target tape is to remain in its position on the back sheet even after the first closing of the diaper.

In a preferred embodiment, the target tape over the closing area completely except for the shear-off securing means. In this way, the largest possible perfect landing zone is automatically made available to the exposed adhesive layer of the closing area. At the same time, the hooks of the closing area are excluded from the coverage by the target tape so that this need be produced to be only as large as necessary.

Regardless of the precise size of the target tape, it is proposed here that this should protrude beyond the user end of the diaper-fastening tape. This proposal is especially understandable when a preferred form of handling of a diaper-fastening tape is used in applying the diaper to the body: according to this variant, the diaper-fastening tape in its original form has three different layers. The first is a fastening carrier. The fastening carrier is a continuous tape that essentially defines the actual size and shape of the diaper-fastening tape. The fastening area and the closing area can be discerned on the fastening carrier. On the fastening tape there is an exposed adhesive layer as the fastening area which runs beyond the entire closing area over the fastening carrier. In the closing area, a hook material is provided on a partial area. Next to the hook material spatially, a target tape is provided, completely covering the adhesive layer of the closing area but leaving the hooks exposed. An adhesive layer is provided on the rear side of the target tape, with an antistick-coated release tape attached to this adhesive layer. The release tape also has an adhesive on its rear side. The release tape ends approximately at the level of the fastening carrier with regard to the direction of the longitudinal extent of the diaper-fastening tape. The target tape protrudes beyond these two ends so that a user initially grip the three-layer arrangement of fastening carrier, target tape and release tape when gripping the end side, i.e., on the free user end.

A release tape is also advantageous independently of a target tape. The diaper-fastening tape can be produced jointed with the release tape or at least supplied in a roll for diaper production. The diaper-fastening tape with its fastening area is permanently attached to a diaper wing of the diaper. The release tape is now arranged in the closing area of the diaper-fastening tape. It serves to hold down the closing area during production, optionally until just before closing the diaper so that there is no loosely protruding end, in particular during production of the diaper. This prevents, for example, a diaper-fastening tape from becoming hooked in the diaper production machine where it could thus damage the diaper.

The connection between the release tape and the closing area here is selected so that the closing area can be gripped easily by a user and released from the release tape.

The release tape preferably covers only the pop-off securing means. In this way, the area for the release tape can be minimized so that the advantages of a release tape are manifested, in particular in conjunction with covering the pop-off securing means, because the release tape in its surface properties can be based in particular on the needs of an adhesive fastening system.

In addition, it is advantageous if the release tape and/or the target tape does not cover the shear-off area because this is usually much thicker than the films of the release tape and/or target tape and the thickness of the diaper-fastening tape and/or a corresponding tape can be equalized in this way. As a result, rolls formed in this way are more stable.

It should be pointed out that the continuous adhesive layer on the fastening carrier need not consist entirely of one material. Instead, according to another aspect of the present invention, it is proposed that the adhesive should change in the longitudinal course of the adhesive layer. For example, the adhesive provided in the fastening area may be such that it enters into a bond only once. An ambient condition may also be required here to achieve bonding, but this is a condition that is not achieved when applying the diaper to the body, e.g., a very hot environment. On the other hand, the adhesive in the closing area may be tailored to be capable of entering into and releasing multiple bonds with the back sheet or with the target tape. The adhesive in the closing area should be pressure-sensitive, so that it can be brought into a bonding connection by the operating person by simply pressing on it.

Cumulatively or alternatively, with a diaper-fastening tape for a mechanical fastening system comprising two components in which the fastening carrier having a fastening area and a carrier area carries one component of the mechanical fastening system in its carrier area, and this component is arranged as an intermediate carrier designed as a spot, which is in turn attached to the fastening carrier and whose edge is arranged obliquely with respect to the direction of the longitudinal extent of the diaper-fastening tape at least in a partial area, it is herein proposed that the diaper-fastening tape shall have an edge carrier which is designed as a edge spot, shall have a component of the mechanical fastening system and shall in turn be attached within the carrier area to the fastening carrier, whereby at the same time it forms a border of the carrier area along an edge section. Therefore, regardless of the other features of the present invention, it is possible to make available diaper-fastening tapes and/or diapers which can be used and fastened especially conveniently and reliably and are also very inexpensive to manufacture.

It should be pointed out that the mechanical fastening system comprising two components may be in particular a hook-and-loop fastener. In this sense, all surfaces capable of cooperating, where arrangements of the one component protruding out of one surface are able to grip behind recesses, loops, openings, fibers or the like of the other component so that this results in a resistance force against separation and/or shearing of the two surfaces. The protruding arrangements of the one component may be in particular hooks or mushroom-head-shaped rods.

The fastening area of the diaper-fastening tape serves to attach same permanently to a surface, e.g., to the wing of the diaper as already explained above. This yields a free end of the tape, the so-called user end. This is where the carrier area is arranged, serving to be guided on a device on the opposing diaper wing that cooperates with the carrier area for closing the diaper after it has been applied by the user to the body and thereby to close the diaper in a reopenable manner. Therefore, the carrier area must reliably absorb the static and dynamic stresses that occur during use of the diaper without becoming opened.

A diaper-fastening tape extends diaper-fastening tape extends from the fastening area to the closing area on the user end of the tape which also comprises the carrier area in its direction of the longitudinal extent. Frequently, a diaper-fastening tape is shaped with a rectangular longitudinal extent. With other shapes, a direction of the longitudinal extent can also be defined if this is arranged perpendicular to the longitudinal direction of the diaper and/or parallel to the extent of a user end of the diaper-fastening tape away from the diaper.

The carrier area is defined by the extent around the surface of the diaper-fastening tape which is furnished for keeping the diaper closed and yet reopenable subsequently after use. Within this area, individual spots of intermediate carriers with components of the fastening system arranged thereon may be provided. For example, US 2003/0009144 A1 describes such a diaper-fastening tape. The intermediate carriers are circular "islands" which are arranged regulator within the carrier area or are positioned randomly. The tape in that patent is essentially rectangular, resulting in a line parallel to the longitudinal edge of the tape running in the direction of the longitudinal extent. The edge of the intermediate carrier is completely oblique with respect to this direction of the longitudinal extent because it is circular in shape. Although this yields two parallel and normal tangents to the direction of the longitudinal extent in running around each individual circular intermediate carrier, the term "partial area" is not understood to include a purely tangential point because it does not have any extent along the edge.

According to the aspect of the present invention explained here, an edge spot having a respective edge intermediate carrier is also provided. This forms a border to the carrier area along a section of its contour.

Through the definition of the carrier area as an area within the border of the spots, the border is also directly adjacent to the islands there in US 2003/0009144 A1 so that these area also in contact with this in spots along a straight extent of the carrier area. As already explained, a spot-wise tangential contact of the spot with the border of the carrier area is not intended here, however. Instead, the border of the carrier area should run along a section of the edge of the spots. The carrier area here is always bordered polygonally so it does not run with a circular arc section of the spot along a corner but instead is in tangential contact exactly twice with a spot circular spot lying on a corner, whereby it shapes a corner between these spots. The carrier may preferably be rectangular in shape.

In comparison with the state of the art, the diaper-fastening tape proposed here is characterized by an especially great shearing and pop-off load-bearing capacity. This is achieved, in particular by the fact that a broader section of the spot extends directly up to the limit of the carrier area. Therefore, great forces can also be mobilized at the limit of the carrier area. This reliably prevents a gradual peeling away of the two components from one another.

In addition, the diaper-fastening tape designed in this way can be manufactured especially easily by manufacturing numerous spots in the machine direction and then cutting through at least a few of these spots when cutting the individual tapes. In this case, an edge spot may advantageously be arranged in such a way that the edge section forming the border of the carrier area is also at the same time situated above the edge of the diaper-fastening tape.

It should be pointed out that one and the same spot may be the intermediate carrier and the edge carrier at the same time. However, it is preferably if one or more edge spots, each having separate carriers, are provided in addition to one or more central spots.

If a hook-and-loop fastening system is used as the mechanical fastening system, then the hooks or loops of the components in the carrier area will usually be arranged in the form of a regular grid. Owing to the simple production process, this grid is usually aligned with its axes parallel or perpendicular to the direction of longitudinal extent. This is also disclosed in US 2003/0009144 A1 so that the edge of the islands due to its circular shape from the grid regularity with the two main directions deviates completely.

Cumulatively and/or alternatively, in deviation from the US 2003/0009144 A1, it is proposed that not only spot edges that deviate from regularity but also an edge section of a spot that runs with regularity are both provided. With a view to simple manufacturing of grid structures within the mechanical components, it is proposed that the regular edge section of the spot shall be straight. Such a spot can be achieved especially easily as an edge spot by the manufacturing method described briefly above. In this way, hooks in particular come to lie in different layers in the edge area and are even partially severed through or cut all the way through. This necessitates much greater holding forces of these hooks in particular, so that even the holding forces of the overall arrangement are greatly increases in comparison with traditional arrangements.

An especially great resistance to separation of the two components of the mechanical fastening system is obtained when at least as many edge carriers are provided in the carrier area as intermediate carriers otherwise.

To design the mechanical behavior of the carrier area to be as isotropic as possible, the spots within the carrier area may be designed to be geometrically similar or even to coincide. This may refer at least to the central spots, i.e., the spots not including the edge spots. Within the context of the present patent application, however, the edge carriers that have a shape according to a part of a central spot should also be considered as geometrically similar or coinciding. Such a shape is obtained, for example, due to the fact that starting from the shape of a central spot, a piece is cut away from it. The central spots may be circular, for example, while the edge spots have the contour of an arc of a circle and its chord.

Since high forces can be accommodated, in particular if the longest possible edge sections of the edge spots are at the border of the carrier area, in the case of circular central spots it is therefore proposed that at least one edge spot shall be designed as a semicircle and shall lie with its chord running through the midpoint of the semicircle along the border of the carrier area.

An especially good compromise between the dependability of the diaper-fastening tape in the carrier area and great holding forces is achieved by means of spots which constitute less than one-third of the width of the carrier area perpendicular to the direction of the longitudinal extent but constitute more than one-fifth of the length of the carrier area parallel to the main direction of extent.

To prevent separation of the two components of the fastening system as much as possible, an intermediate space between the spots, as already described above in detail, may have an exposed adhesive layer. In particular, the entire intermediate space between the spots may have such a surface property. A very handy user end is obtained on the diaper-fastening tape when the exposed adhesive layer is limited to the carrier area which is bordered by the edge spots.

Regardless of any adhesive layer, the spots may advantageously have their own main direction of extent. A spot has its own main direction of extent when it has a perceptible or pronounced two-dimensional structure with an at least essentially one-dimensional extent. Then the main direction of extent is the direction running along the main axis of the spot area by which the spot area has the smaller moment of inertia per unit of area. With such an elongated spot, a buckling line may easily be provided next to and parallel to it. A buckling line within the context of the present patent application is considered to be a straight or essentially straight segment running between two bordering points of the carrier area that are preferably a distance apart and do not intersect any spot having an intermediate carrier. The intermediate carriers are generally relatively hard and thus inflexible components made of plastic. If the user end of the diaper-fastening tape has one or more buckling lines, it appears to be very flexible on the whole in the user's hand and may conform in the best possible way to deformations in the mating component when the item is being worn.

In order that a diaper-fastening tape having a buckling line of the type described above will execute only relatively controllable movements and will nevertheless remain stable with all its flexibility, a bending line or a set of bending lines may advantageously be situated approximately perpendicular to or at an angle of approximately 45° to the direction of longitudinal extent. Regardless of the precise alignment, it is proposed that buckling lines in only one direction or at least essentially only in one direction lie in the carrier area so that a very good closing force and an adequately high bending possibility are created, which lead to a high fastening force against shearing forces because the buckling lines run obliquely, e.g., shearing forces such as those which occur precisely with a closed diaper-fastening tape which is under tensile stress. On the other hand, the buckling lines may be omitted entirely when using spots so the great overlapping of the spots, in particular in the direction of longitudinal extent of the diaper-fastening tape, also results in a high fastening force against shearing forces and nevertheless ensures a high mobility of the diaper-fastening tape in the carrier area as well due to the use of individual spots.

If there are no buckling lines in the carrier area, this area is nevertheless relatively flexible per se when using the spots, whereas the border of the carrier area has very little flexibility. This results in a very controlled haptic feedback when gripping the diaper-fastening tape and may therefore be perceived by the user as very pleasant.

Cumulatively and/or alternatively, it is proposed that no buckling line through the carrier area results in the case of a diaper-fastening tape for a mechanical fastening system comprising two components, wherein a fastening carrier with a fastening area and a carrier area carries one component of the mechanical fastening system in its carrier area, and this component is arranged on an intermediate carrier as a spot, which is in turn fastened to the fastening carrier and whose edge is arranged obliquely in at least a partial area with respect to a direction of the longitudinal extent of the diaper-fastening tape whereby with this system with which the intermediate carrier is divided in both the longitudinal direction and the transverse direction the intermediate carrier is divided in both longitudinal and transverse directions. The holding force can also be greatly increased in this way because significantly more hooks, i.e., male components can be intensely engaged with the loops, i.e., the female components.

In particular when a buckling line is provided but not limited to this case, it is advantageous if the partial area of the spot extends with the oblique edge over an entire width of the diaper-fastening tape perpendicular to the direction of the longitudinal extent. In this way strip-shaped spots in particular can be produced especially easily because a continuous strip having an oblique edge can easily be applied over several tapes in the machine direction, i.e., normal to the direction of the longitudinal extent of the tape, whereby the continuous strip is also severed when cutting through the individual tapes. The oblique edge of such a strip may have a corrugated shape or a zigzag shape, for example.

It should be pointed out that such a diaper-fastening tape having a spot with an oblique edge, whereby this oblique edge of the spot extends over the entire width of the tape, preferably with two alternating directions of running, is also advantageous and inventive regardless of all the other features of the present invention.

The carrier area of the diaper-fastening tape is especially stable when a projection of the spots onto a straight line which is situated in the plane of the tape and normal to the longitudinal direction of extend and/or parallel to the direction of the longitudinal extent yields numerous different overlappings of projections of spots. In particular it is advantageous if the spots are arranged so that spots that are scattered normal to the projection lines in the carrier area as well as spots that are arranged essentially parallel to the projection lines with a distance from one another in the carrier area intersects in the projection.

A diaper-fastening tape that is very stable in use is obtained independently of what is said above if the intermediate carrier is designed as a spot which has a varying edge in the machine direction whereby, when seen in the direction of the longitudinal extent, at least one spot is present at each level running in the machine direction over the effective width of the carrier area. In other words, this is the case when no buckling line runs parallel to the direction of the longitudinal extent through the carrier area; described in plastic terms, there is thus no gap between the spots in the direction of view along the direction of the longitudinal extent of the tape.

Such a condition can be achieved especially easily by the fact that the varying edge of a spot already extends over the entire height of the diaper-fastening tape in the machine direction.

On one border of the carrier area, such a spot may advantageously have an edge section with a straight course.

Outside of the carrier area, one or more adhesive surfaces may be provided to keep a release tape in use readiness, for example.

Accordingly, a diaper-fastening tape for a mechanical fastening system comprising two components is also proposed, wherein the intermediate carrier is designed as strip-shaped spots by means of a separation in a first direction and by a weakening at a distance in a second direction. This is to be understood by the fact that the intermediate carrier is completely separated into two or more strips along the first direction, whereby the strips are essentially parallel to the first direction and to one another. In the second direction, i.e., along the course of the strips, they are provided with an edge variation, e.g., preferably regular weakened spots arranged a distance apart, representing in particular a constriction of the strip, i.e., a narrowing of its width. In this way, pronounced buckling lines are formed along the first direction, i.e., along the dividing lines of the individual strip-shaped spots. On the other hand, weaker but still perceptible additional buckling lines are also formed approximately perpendicular to the former. Therefore, independently and/or in addition to the other features of the present invention, the holding forces may also be increased thereby in such a diaper-fastening tape.

If the edge variation and/or the weakening in the strip-shaped spots is/are made perpendicular to the plane of the tape, this yields the weak buckling lines as parallels to the direction of the longitudinal extent of the tape. However, if the edge variations and/or the weakenings are instead or additionally at the site of the strip-shaped spots within the plane of the tape, this results in a set of weak buckling axes perpendicular to the plane of the tape.

To be able to absorb forces in the best possible way, the edge of a strip-shaped spots may be shaped obliquely with respect to a direction of the longitudinal extent of the diaper-fastening tape in at least a partial area.

An edge section running in a straight pattern on the strip-shaped spot may preferably be provided on a border of the carrier area so as to achieve a high uptake of force there in the manner described above.

With such strip-shaped spots, an exposed adhesive layer may also be provided between the spots to improve the adhesive effect with respect to the other component of the fastening system.

An especially homogenous behavior of the carrier area is achieved if several strip-shaped spots that coincide are provided within the carrier area. The partial area with the oblique edge may also extend over the entire width of the diaper-fastening tape perpendicular to the direction of the longitudinal extent.

Numerous possible embodiments according to the previous discussion can be achieved especially practically by making targeted cuts through spots at the time of manufacture if the individual diaper-fastening tapes are separated from one another in the machine direction. A cut through a spot automatically results in an edge spot having a corresponding extent of the fastening component along the edge of the carrier area. The edge of the carrier area in this case coincides with the longitudinal edge of the diaper-fastening tape.

It should be pointed out that the aforementioned advantages are effective, in particular when an inventive diaper-fastening tape is applied to a diaper.

All the aspects with regard to the spots are presented above are based on the fundamental idea of influencing the flexibility of the carrier area in a targeted manner and/or influencing the transfer of force between the mechanical fastening components through the geometric design of the spots. Through oblique edges of the spots within the plane of the tape, the tensile forces running in the direction of the longitudinal extent of the tape can be introduced into the fastening system so that the fastener remains closed more reliably during use. Due to the targeted divisions, weakenings, buckling lines and areas free of intermediate carriers, the flexibility of the corresponding component of the mechanical fastening system is greatly increased so that this component can be adapted better to its counterpart and in particular can interact with it better. In this case, the flexibility is controlled to a significant extent by the flexibility of the fastening carrier which can usually be designed to be much more flexible than the intermediate carrier.

Due to the fact that the edge of the spot varies in the machine direction, the flexibility of the carrier area is also increased and this ensures that the component provided on the spot and/or on several spots can interact in the great possible variety of ways so that the total fastening force is further increased.

Within the context of the present patent application, the term "machine direction" describes the direction with which a diaper-fastening tape usually runs through a machine during production, during which it is usually severed perpendicular to this direction. The term "direction of the longitudinal extent" describes a direction running from the fastening area to the carrier area, normally running perpendicular to the machine direction.

When severing at least some of the hooks and/or the protruding arrangements in the production of a fastening tape or a spot carrying the hooks and/or the arrangements, these components then have sharper edges than in their original state. In this way, the hooking engagement properties and thus the overall fastening forces are further increased.

Regardless of the preceding discussion but also in addition thereto, it is advantageous if in the case of a diaper with a diaper-fastening system and a hook-and-loop fastening system, whereby the hooks are worn in the carrier area of the diaper-fastening tape, the loops are formed directly by a nonwoven on the back sheet of the diaper. In this way, a cost intensive separate component having loops as part of the fastening system may be omitted.

It is self-evident that the advantages of the aforementioned aspects of the present invention with regard to a fastening tape also extend directly to a tape material having a direction of the longitudinal extent whereby the tape material can be divided by cutting it across the direction of the longitudinal extent and optionally also essentially in the direction of the longitudinal extent to yield individual uses—preferably without any waste—in the form of fastening tapes of the described type. The individual uses preferably come from the manufacturer in the form of a cohesive tape material.

The same thing is also true analogously for a winding, in particular a roll or a reel of such a tape material. The same thing is also true of a diaper having such a diaper-fastening tape.

Figure 2:
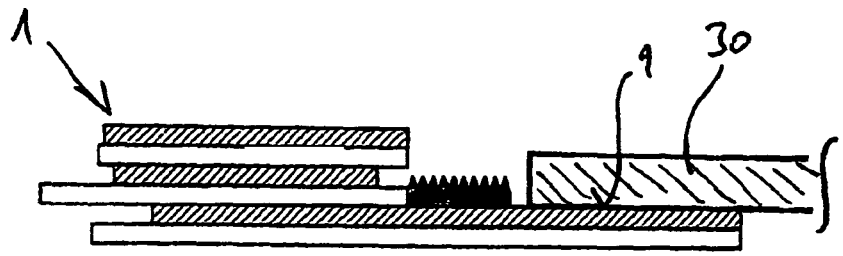
Figure 3:
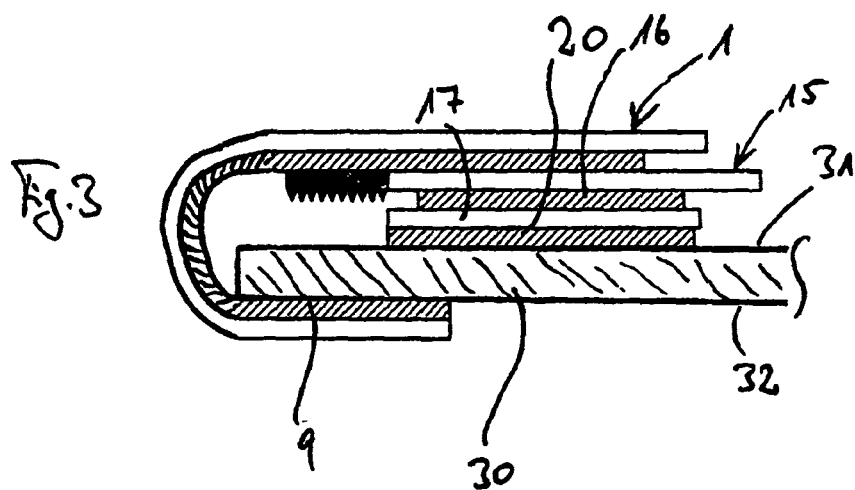
Figure 4:
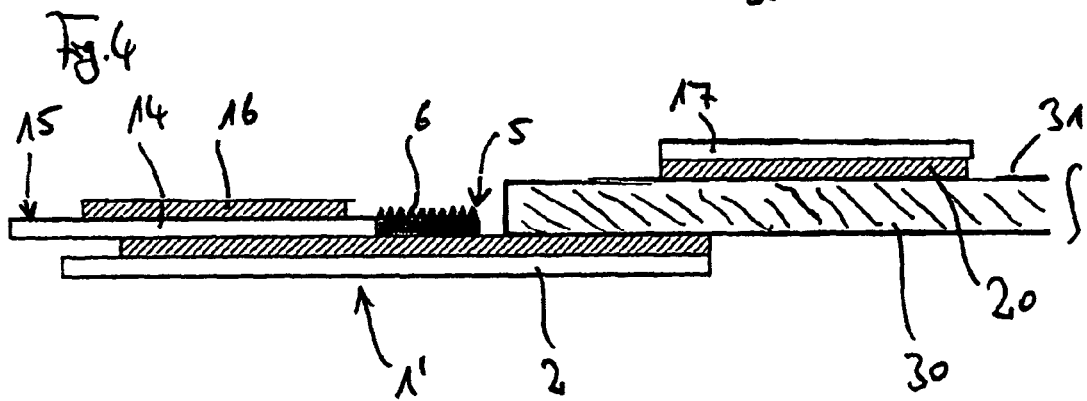
Figure 8:
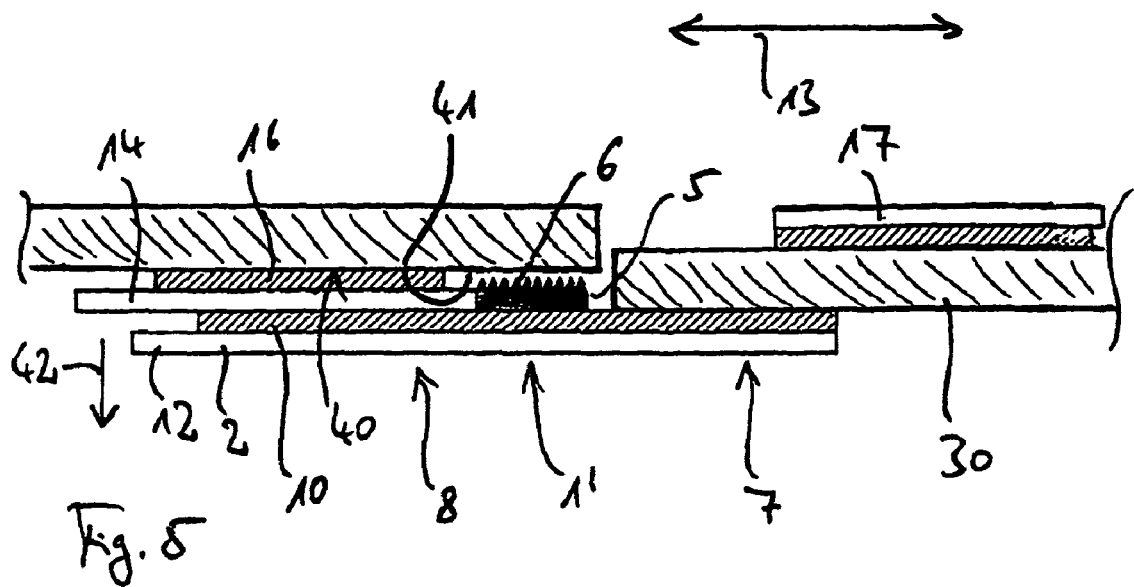
Figure 16:
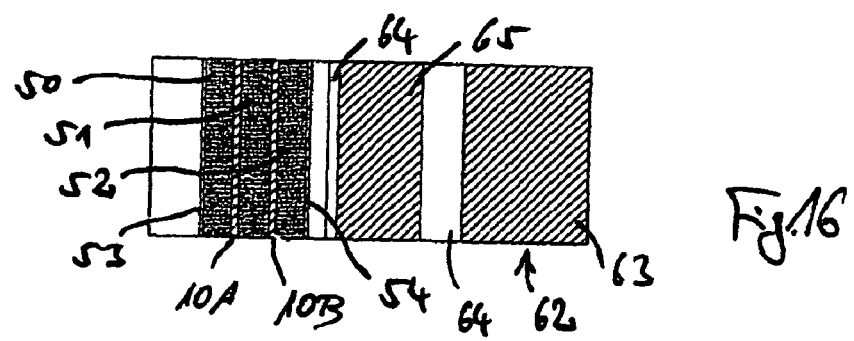
Figure 6:
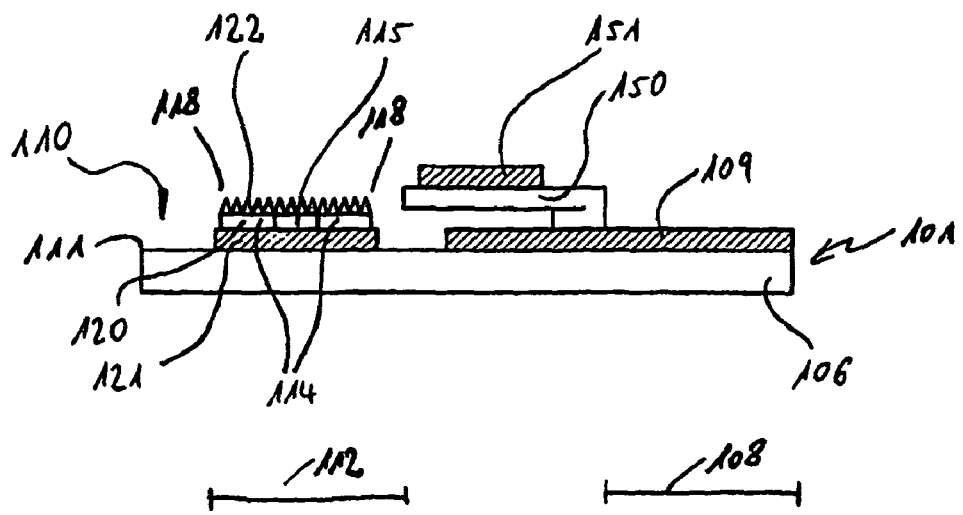
Figure 7:
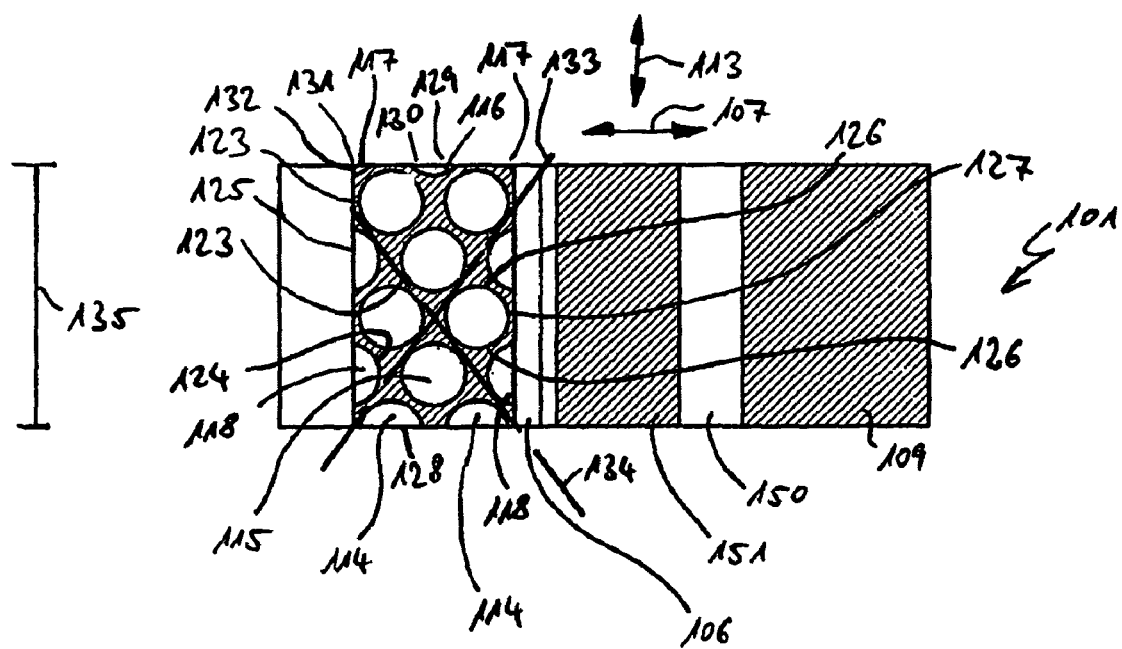
Figure 8:
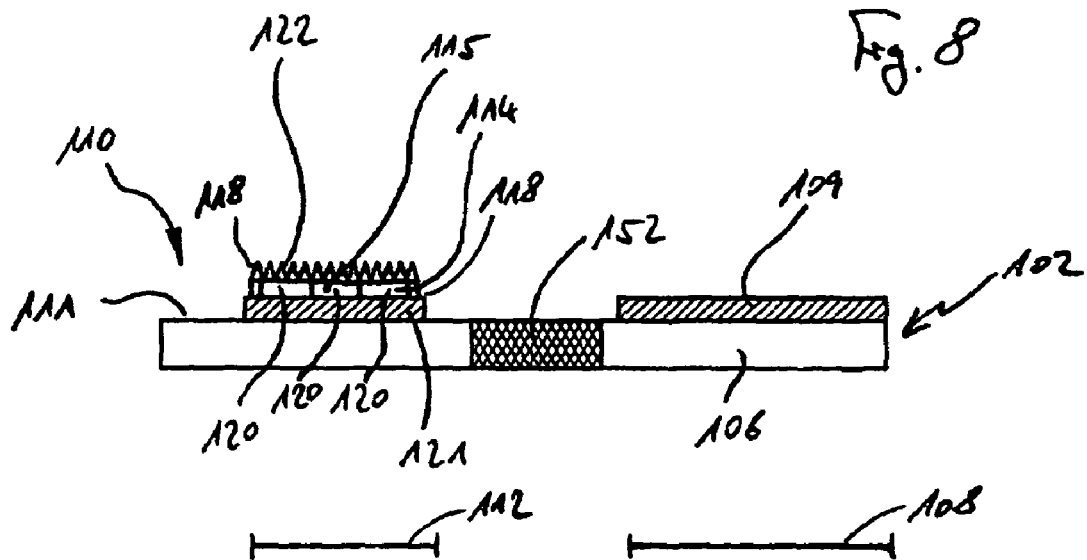
Figure 9:
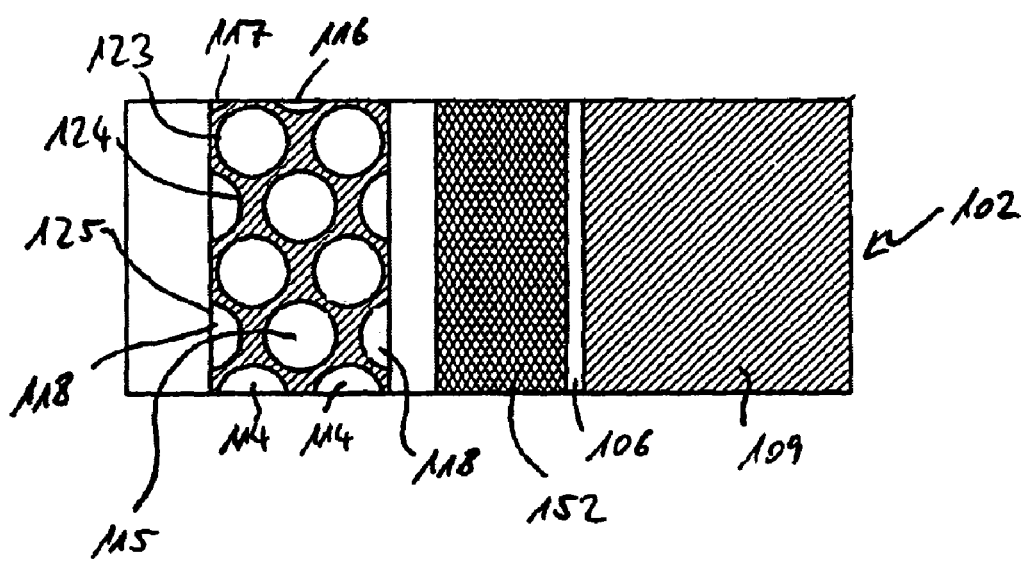
Figure 10:
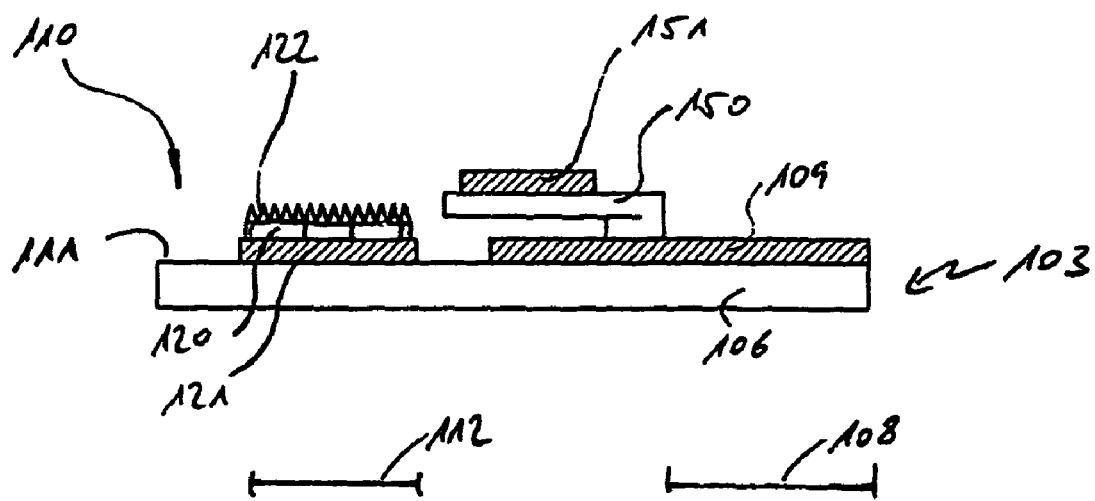
Figure 11:
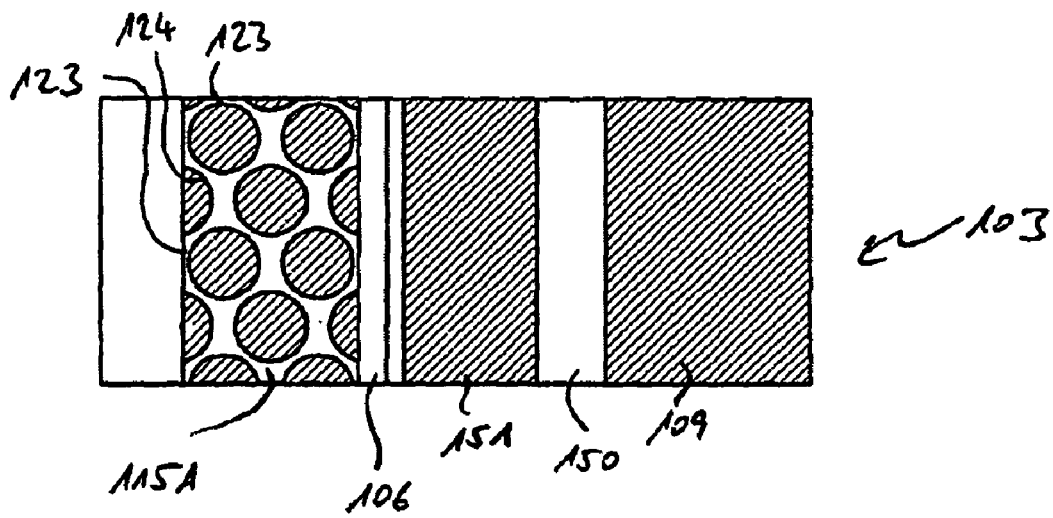
Figure 12:
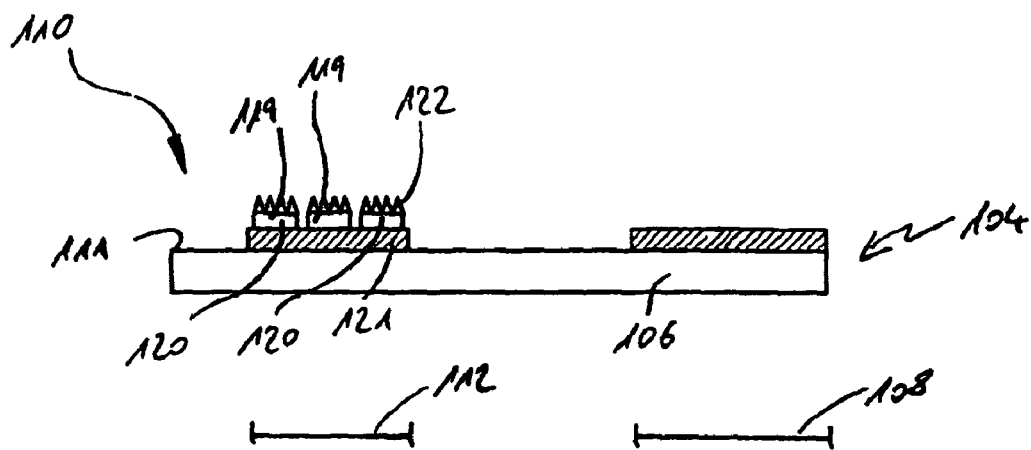
Figure 13:
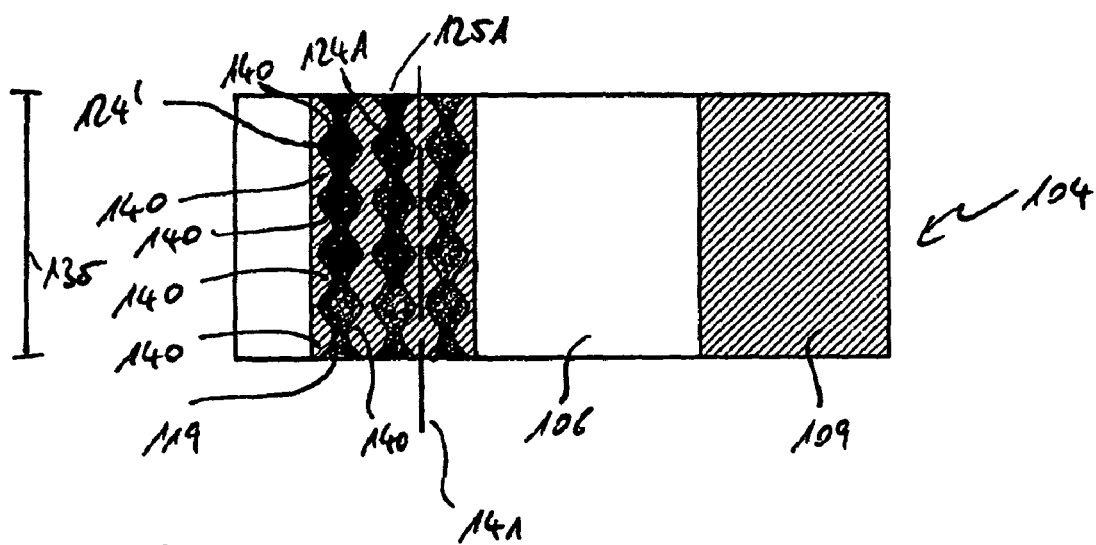
Figure 14:
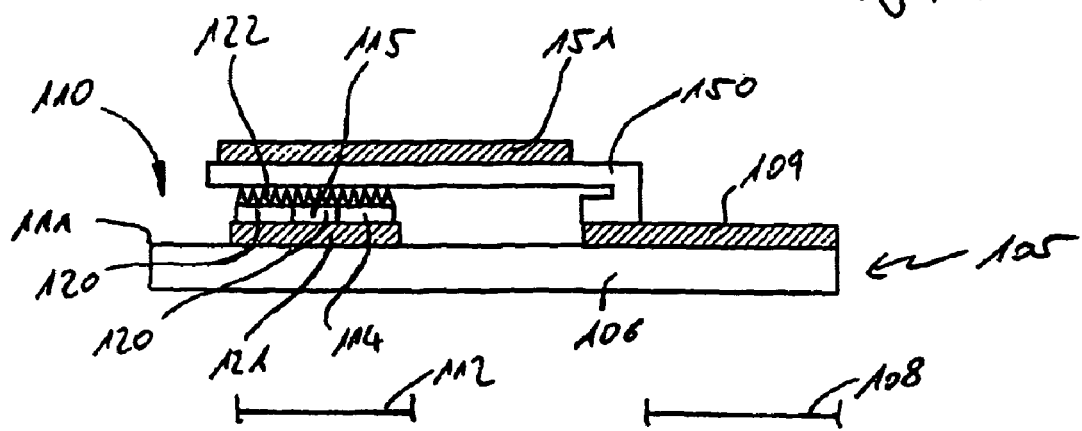
Figure 15:
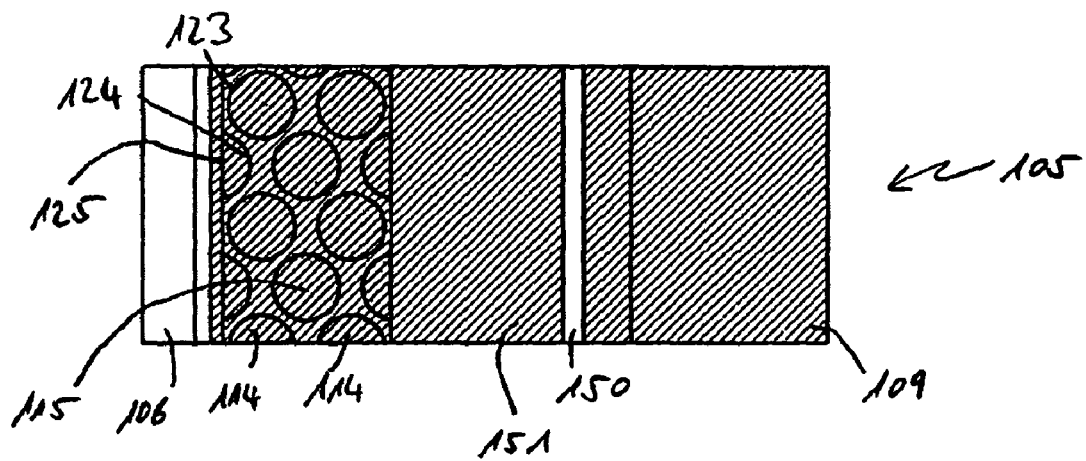

This invention is explained in greater detail below on the basis of several exemplary embodiments with reference to the drawing. Functionally identical components are labeled with the same reference numerals in the drawing, in which FIG. 1 shows schematically in a side view a diaper-fastening tape which embodies several aspects of the proposed invention, FIG. 2 shows the diaper-fastening tape from FIG. 1, applied to diaper wing in a second processing step, FIG. 3 shows the diaper-fastening tape from FIGS. 1 and 2 in a third processing step for attaching to the wing of the diaper from FIG. 2, FIG. 4 shows the diaper-fastening tape from FIGS. 1 through 3 in a fourth processing step, FIG. 5 shows the diaper-fastening tape from FIGS. 1 through 4 in a fastener configuration, applied to the wing of the diaper from FIGS. 2 through 4 and detachably attached to a landing zone and FIG. 6 shows schematically a side view of a first diaper-fastening tape, FIG. 7 shows the diaper-fastening tape from FIG. 1 in a view from above, FIG. 8 shows schematically a second diaper-fastening tape in a side view, FIG. 9 shows the diaper-fastening tape from FIG. 3 in a view from above, FIG. 10 shows schematically a third diaper-fastening tape in a side view, FIG. 11 shows the diaper-fastening tape from FIG. 5 in a view from above, FIG. 12 shows schematically a fourth diaper-fastening tape in a side view, FIG. 13 shows the diaper-fastening tape from FIG. 7 in a view from above, FIG. 14 shows schematically a fifth diaper-fastening tape in a side view, FIG. 15 shows the diaper-fastening tape from FIG. 9 in a view from above and FIG. 16 shows schematically a sixth diaper-fastening tape in a view from above.

The diaper-fastening tape 1 in FIG. 1 consists essentially of a tape-like fastening carrier 2 with an adhesive layer 4 provided on its surface 3. The adhesive layer in turn has a hook spot 5 having numerous small hooks (represented by jags and labeled with 6 as an example).

The hook spot 5 divides the diaper-fastening tape 1, more specifically the fastening carrier 2, into two areas: first a fastening area 7, secondly a closing area 8. The fastening area 7 is intended for being attached permanently to a wing of a diaper. When attached to the wing of the diaper, the diaper-fastening tape 1 is guided its exposed adhesive surface 9 toward the back sheet material of the diaper in such a way that the hook spot 5 remains free and thus protrudes laterally beyond the wing of the diaper.

The closing area 8 serves to keep the diaper to whose wing the diaper-fastening tape 1 is attached, detachably closed for a certain period of time. The hooks 6 and/or exposed adhesive surface 10 of the adhesive layer 4 running continuously from the fastening area 7 to the closing area 8 therefore enter into a detachable connection with the surface of the hygiene item. To this end, a landing zone is created on the surface of the hygiene item. The diaper-fastening tapes of the type illustrated here are usually attached to both wings of the section of a diaper at the rear when the diaper is being worn; then the diaper is applied to the body and in doing so the front section of the diaper is placed in front of the abdomen. Then the landing zone is usually provided on the outside of the front section.

In disposing of the diaper, it is usually folded differently than it is while being worn. Therefore, the diaper-fastening tapes are usually at a different spot on the diaper when closing the diaper for disposal.

Due to the fact that the hook spot 5 is merely placed on the continuous adhesive layer, this ensures that both the exposed adhesive surface 9 of the fastening area 7 as well as the exposed adhesive surface 10 in the closing area 8 extend directly up to the hook spot 5.

In an alternative embodiment, an intermediate area may also be provided between the fastening area 7 and the closing area 8; this intermediate area does not have any direct connecting function to the diaper per se but increases the distance between the fastening area 7 and the closing area 8 so that the diaper fastener is easier to operate.

On a free user end 11 of the fastening carrier 2, it has a protruding section 12 that goes beyond the closing area 8.

This hook spot itself belongs to the closing area 8. The hooks 6 of the hook spot 5 are small elastically flexible hook having the usual shape associated with a hook and -loop fastener such as that described in US 6,210,389 B1, for example. The hooks 6 thus form a male component of a mechanical two-component fastening system namely a hook-and-loop fastening system.

In the longitudinal course of the diaper-fastening tape 1 along a direction of the longitudinal extent 13, the closing area 8 is defined with respect to the free user end 11 by the free adhesive surface 10. Toward the fastening area 7, the closing area is bordered by the hook spot 5. The surface of the exposed adhesive layer 10 greatly exceeds the surface of the hook spot 5. It amounts to approximately three and one-half times the surface area covered with hooks.

A target tape 14 is arranged on the exposed adhesive layer 10 in the closing area 8. The target tape 14 covers the entire exposed adhesive surface 10, extending directly up to the hook spot 5. At the same time, a pointed section 15 of the target tape 14 on the user end 11 of the diaper-fastening tape 1 extends beyond the fastening carrier 2.

A second adhesive layer 16 is provided on the target tape 14. The release tape 17 covers the entire second adhesive layer, extending to the faceting area close to the hook spot 5, but not covering the latter. Toward the user end 11, it also leaves the pointed section 15 of the target tape 14 free.

The release tape is provided with an antistick coating on a surface 18 facing the second adhesive layer 16 so that the bond between the second adhesive layer 16 and the release tape 17 is much weaker than the bond between the second adhesive layer 16 and the target tape 14 and is much weaker than the bond of the exposed adhesive layer 10 and the target tape 14.

On a rear side 19, the release tape has a third adhesive layer 20 which covers the release tape 17 almost completely. A cover strip 21 is provided on the third adhesive layer 20, completely covering the hook spot 5 in a projection onto the plane of the fastening carrier 2 and thus onto the plane of the entire diaper-fastening tape 1.

The diaper-fastening tape 1 may be cut from a tape material in the form shown in FIG. 1 as an individual use item.

FIG. 2 shows the diaper-fastening tape 1 with the exposed adhesive surface 9 arranged on one edge of a wing 30 of a diaper (shown only partially here). At the same time, the covering strip 21 is removed so that attaching the diaper-fastening tape 1 and further handling are facilitated.

In the third processing step, the diaper-fastening tape 1 is folded around the edge of the wing 30 of the diaper (shown disproportionately since the drawing has not been done to scale with regard to the size ratios). The third adhesive layer 20 is engaged with an inside 31 of the back sheet 30. At the same time, the diaper-fastening tape 1 is permanently secured on the outside 32 of the back sheet 30 via the adhesive surface 9. In this form, the diaper-fastening tape 1 is extremely compact on the wing 30 of the diaper. The diaper can be processed further with no problems.

In the initial use, the actual diaper-fastening tape 1', defined by the fastening carrier 2 is separated from the release tape 17. This may be accomplished easily by gripping the diaper-fastening tape 1' on the pointed section 15—starting from the constellation as illustrated in FIG. 3—and removing it from the back sheet 30. The connection of the second adhesive layer 16 to the release tape 17 is relatively weak, as already explained. Consequently, the release tape 17 with the third adhesive layer 20 remains on the inside 31 of the back sheet 30. The remainder 1' of the diaper-fastening tape 1 may be gripped as the protruding tape and used.

In the constellation after the step according to FIG. 4, the second adhesive layer 16 is now exposed. The hooks 6 of the hook spot 5 are also open and are in relatively close proximity to the second adhesive layer 16.

In the open configuration according to FIG. 4, the closing area can now be applied to a landing zone on the back sheet. This yields the fastener configuration according to FIG. 5.

In the fastener configuration in FIG. 5, the landing zone 40 of the back sheet of the diaper is attached to the second adhesive layer 16 after this was lying open after the fourth step. By pressing on the closing area 8 of the diaper-fastening tape 1' against the landing zone 40, the target tape 14 is connected via the second adhesive layer 16 to the landing zone 40, and the hooks 6 of the hook spot 5 become engaged in fibers (not shown) of a nonwoven as the back sheet of the diaper on an outer surface 41 of the landing zone 40. A friction locking connection is thus established after sufficiently secure pressing over the area in the closing area 8 against the landing zone 40 by the cooperation of adhesive forces 16 and hooking forces 6. The hooks 6 engage in the surface of the nonwoven at the surface 41.

The diaper-fastening tape 1', more specifically its closing area 8, is secured twice in the fastener constellation according to FIG. 5. Toward the fastening area 7, the mechanical hook-textile back sheet connection initially creates a strong means of securing the diaper against shearing ("shear-off"). When shear-off occurs, the two parts of the back sheet of the diaper are removed perpendicular to the plane of the drawing and/or along the direction of the longitudinal extent 13.

The adhesive bond of the fastening carrier 2 via the adhesive layer 10, the target tape 14, and the second adhesive layer 16 with the surface 14 in the landing zone 40 secures it in particular so that the closing area 8 does not spring away (pop off) from the landing zone in a direction 42 so it cannot become loosened from the surface 41. At the same time, this pop-off securing means causes the hooks 6 to be held in the surface 41 of the landing zone 40 so that the shear-off securing means remains reliably active. Shear-off is the main force load to be expected for the fastener of the diaper.

The adhesive bond between the target tape and the landing zone 40 due to the second adhesive layer is stronger than the adhesive bond between the adhesive layer 10 and the target tape 14. As a result, the closing area 8 of the diaper-fastening tape 1' can easily be pulled away from the target tape 14 in the closing constellation 5, once it has been attached. To do so, the free protruding section 12 in particular on the user end 11 of the diaper-fastening tape 1' can be gripped and pulled away from the landing zone 40 in the pop-off direction 42. After pulling away the adhesive connection, the hooks 6 are also pulled out of the landing zone 40 by further pulling along the direction 42 so that the diaper is reopened.

This procedure is completely reversible. To close the diaper again, the closing area 8 of the diaper-fastening tape 1' is brought back to the landing zone 40 in the direction opposite the pop-off direction 42. This landing zone is now permanently provided with the target tape 14. Thus in the detail, the exposed adhesive layer 10 is simply brought to the target tape 14 and pressed against it, whereby not only the adhesive bond is re-established by consistent flat pressure but also the hooks 6 are pressed again into the surface 41 of the landing zone 40. Then the connection of the two parts of the diaper is again securely established.

The double-acting fastening securing means achieves a resistance to opening forces which ensures a high reliability of the diaper fastener. Depending on the design, pop-off forces between 0.5 N and 35 N can easily be absorbed by a tape having a tape width of 25 mm. These values are based on ambient parameters of 23° C.±2° C. and 50%±5% relative atmospheric humidity, whereby the tape is pulled away with a pull-off rate of 200 mm/min perpendicularly to the plane of the connection over the entire hook area after the entire area has been pressed with a force of 20 N.

With regard to the dynamic shearing strength, resistance forces between 0.5 N and 40 N have easily been determined on a 25 mm wide tape, assuming a draw-off rate of the tape of 300 mm/min within the plane of the connection after the connection has been established with a pressure of 20 N over the width of the tape at a rate of 300 mm/min—once forward and once in reverse over the connection.

It should be pointed out that the aspects of the invention presented here are independent of one another. The diaper-fastening tape 1 in FIGS. 1 through 5 embodies several aspects of the invention simultaneously. For example, the hook spot 5 takes up only a small part of the closing area 8. In addition, the closing area 8 has, starting from the fastening area 7, first the shear-off securing means in the form of the hook spot 5. In addition, there is a separable target tape 14 on the closing area 8 which partially covers it, namely precisely the part that is provided with the exposed adhesive layer 10, whereby it leaves the shear-off securing means in the form of the hook spot 5 completely exposed. However, the tape would manifest its strength of the double function mechanism even if, for example, this separable target tape were not provided and only the closing area 8 with its hook 6 and the adhesive surface 10 were to be pressed directly onto a textile surface 41 in the landing zone 40.

In addition, it should be pointed out that the closing area 8 need not be divided, strictly speaking, into precisely a mechanically acting shear-off securing means and a pop-off securing means that acts by way of adhesive. Instead, each of the two surfaces may also be divided. In particular, there may even be repeated changes between coated zone, completely uncoated zone and hook zone.

The diaper-fastening tapes in FIGS. 12, 13 and 16 embody such variants. The tapes in FIGS. 12, 13 and 16 each carry three strips 119 and/or 50, 51, 52 with hook material in the closing area, while an exposed adhesive layer 121 and/or 10A, 10B is presented between them. The two tapes also have two small edge strips 121 and/or 53, 54 with exposed adhesive in the closing area. In the case of the diaper-fastening tapes in FIGS. 6 through 11 and 14, 15, there are hook areas in the form of a hole grid and/or in the form of punched blanks, whereby an exposed adhesive layer is presented between the hook areas, as explained below in detail.

The five diaper-fastening tapes 101, 102, 103, 104, 105 according to FIGS. 6 through 15 each consist essentially of a rectangular fastening carrier 106 on which functional elements are arranged. The fastening carrier 106 has an elongated shape and therefore has a direction of the longitudinal extent 107.

In a fastening area 108, an exposed adhesive layer 109 is arranged on the fastening carrier 106. When attaching one of the diaper-fastening tapes 101, 102, 103, 104, 105 to a diaper in its production, the adhesive layer 109 of the fastening area 108 serves to permanently secure the diaper-fastening tape 101, 102, 103, 104, 105 on the surface of the diaper, usually on the wing of the diaper.

However, the area which is to be gripped by the user when applying the diaper to the body is situated on a free end 110 of the diaper-fastening tape 101, 102, 103, 104, 105. This area is also referred to as the finger lift or user end, where the term finger lift frequently is also used to refer only to a free protruding edge 111 of the fastening carrier 106 that protrudes beyond the function elements.

A carrier area 112 is provided on the user end 110 of the diaper-fastening tape 101, 102, 103, 104, 105. The carrier area 112 in these exemplary embodiments extends over the total width of the diaper-fastening tape 101, 102, 103, 104, 105 in the machine direction 113. The carrier area 112 is defined by a bordering edge around the spots 114, 115, 116, 117, 118, 119 (labeled with numbers as examples, whereby the spots 114, 115, 116, 117, 118, 119 each have an intermediate carrier 120 (labeled with numbers as examples) which is attached by an adhesive bond 121 to the fastening carrier 106. On the intermediate carrier 120, there are also hooks 122 (labeled with numbers as examples) which form a component of a hook-and-loop fastening system.

The carrier areas 112 of the diaper-fastening tapes 101, 102 and 105 in FIGS. 6, 7, 8, 9, 14 and 15 are identical with regard to the design of the spots; thus, all the spots 114, 115, 116, 117, 118 are full circles or sectors of circles while the carrier areas 112 of the diaper-fastening tape 103 are complementary thereto in FIGS. 10 and 11. In the first exemplary embodiments, six full-circle central spots 115 are situated within the carrier area 112. Four semicircular spots 118 are situated on a longitudinal edge of the carrier area 112 and thus perpendicular to the longitudinal direction of the longitudinal extent 107. Thus two edge spots 114 which are also semicircular and/or an edge spot 116 constituting less than a semicircle and two edge spots 117 constituting less than a quarter circle are situated on the end sides of the carrier area 112 and thus above a longitudinal edge of the fastening carrier 106. The central spots 115 are shaped to coincide with one another. The edge spots 114, 116, 117, 118 are sectors of circles having the same radius with regard to one another and with regard to the central spots 115. The midpoints of the circles of the central spots 115 and the edge spots 114, 116, 117, 118 are arranged in a uniformly shaped grid so that spot edges 123, 124, 125 (labeled with numbers as examples) form a uniform pattern within the carrier area 112.

The spot edge 123 of the central spot 15 thus describes a complete circle. To this extent the spot edge 123 of the spot is completely oblique with regard to the direction of the longitudinal extent 107 of the diaper-fastening tape 101, 102, 105.

When considered in detail, there is a tangent parallel (quadrant points 126) and/or perpendicular (quadrant points 127) to the direction of the longitudinal extent 107 on the quadrant points 126, 127 (labeled with numbers as examples. When considered in detail, however, this is the case at only the four quadrant points 126, 127 with a theoretical edge segment of zero. To this extent, it is impossible to speak of a partial area of the edge 123 of the spot not running obliquely to the direction of the longitudinal extent 107.

The semicircular edge spots 114, 118 thus have a spot edge 124 running obliquely to the direction of the longitudinal extent 107 as well as a straight edge section 128 (labeled with numbers as examples). Along the outer course of the semicircle, the spot edge 124 is thus completely oblique to the direction of the longitudinal extent 107 while the edge section 128 which is identical to the diameter of the edge spots 114, 118 is completely straight and in the case of the spots 114 is parallel with the direction of the longitudinal extent 107 and/or in the case of the edge spots 118 it is normal to the direction of the longitudinal extent 107.

The edge spot 116 likewise has a spot edge 124 which is in the shape of an arc of a circle but is smaller than that of the semicircular edge spot 114, 118. The edge spot 116 is bordered along a chord 129. The chord 129 forms an edge section 130 as the straight spot edge 125 of the spot 116 in the same way as the edge sections 128, which are the length of one diameter, of the semicircular edge spots 114, 118.

The corner edge spots 117 like the central spots 115 and the other edge spots 114, 116, 118 have an arc-shaped spot edge 124 but also have two straight-edge sections 131, 132 on the spot edge 125 that are mutually perpendicular. The edge sections 131, 132 are parallel or perpendicular to the direction of the longitudinal extent 107 of the diaper-fastening tape 101, 102, 105 while the arc-shaped partial area is situated completely oblique to the direction of the longitudinal extent 107.

The edge sections 128, 130, 131, 132 of the edge spots 114, 116, 117, 118 aligned parallel or perpendicular to the direction of the longitudinal extent 107 are situated on each edge of the carrier area 112 aligned in rows together so that the carrier area 112 yields an exact rectangle. All the straight sections of the spot edges 123, 124, 125 in these exemplary embodiments are situated on the border of the carrier area 112 and thus form the border of the carrier area along the respective edge sections 128, 130, 131, 132. However, all the oblique partial areas of spot edges 124 and/or all the completely oblique spot edges 123 are inside the border of the carrier area.

The circular central spots 115 each have an intermediate carrier 120 which is also circular while the edge spots 114, 116, 117, 118 have an intermediate carrier that has been cut off and has at least essentially the shape and size of the respective edge spot. The adhesive layer 121 runs continuously within the entire carrier area 112 beneath the spot-shaped intermediate carrier 120 within the entire carrier area 112. Therefore, the adhesive layer 121 is exposed between the spots 114, 115, 116, 117, 118. All the spots 114, 115, 116, 117, 118 are provided with hooks 122 in a very fine grid-like arrangement. The grid of the hooks 122 is aligned with its main axes parallel or perpendicular to the direction of the longitudinal extent 107.

The components that have been cut off with respect to the circular intermediate carriers for carrying the hooks 122 of the edge spots 114, 116, 117, 118 are therefore round carriers according to the shape of the spot which also extend, like the spots, up to the edge of the carrier area 112.

The carriers of the edge spots 114, 116, 117, 118 function—in the wording of the patent claims—both as intermediate carriers and as edge carriers because they have an oblique partial area 124 on their edge as well as an edge section 125 which forms a border of the carrier area 112.

The size of the spots 114, 115, 116, 117, 118 is selected so that approximately four complete spots 115 can be arranged within the carrier area and thus on the diaper-fastening tape perpendicular to the direction of the longitudinal extent 107. At the same time, approximately two to three complete spots 115 can be arranged within the carrier area 112 along the direction of the longitudinal extent 107. This choice of sizes yields relatively highly extended spots 115 which thus impart a relatively great strength to the user end 110 of the diaper-fastening tape 101, 102, 105.

These spots are at the same time designed to be so small in their regular arrangement and/or arranged with regard to one another so that three straight buckling lines are formed along a first direction 133 and a second direction 134 (for reasons of simplicity, only the longest buckling line thus formed is shown here). The two directions 133, 134 of the buckling lines are arranged obliquely to the direction of the longitudinal extent 107. Since neither of the two directions here runs parallel to the direction of the longitudinal extent 107, there are no free segments in a projection of the spots 114, 115, 116, 117, 118 onto a projection line 135 within the projection of the carrier area 112. Instead, there are even numerous overlapping in the projection of the spots.

The machine direction 113 runs perpendicular to the direction of the longitudinal extent 107 and the spots 114, 115, 116, 117, 118—and therefore also the intermediate carriers—have an edge 123, 124 which is arranged obliquely to the direction of the longitudinal extent 107 and varies based on the shape of the arc, so the edges of the spots and thus also the edges of the intermediate carriers also vary with regard to the machine direction 113. Thus there is at least one spot 114, 115, 116, 117, and/or 118 at each level running in the machine direction over the effective width of the carrier area 112, i.e., over the width of the tape 101, 102, 103, 104, 105. Otherwise, there would also be a free zone in the projection onto the projection spot 135. At the same time, there would be a bending line in one direction parallel to the direction of the longitudinal extent 107.

It is likewise possible to select the dimensions or to arrange the spots in such a way that no buckling line through the carrier area 112 is formed. To do so, some or all of the spots could be enlarged. It would also be conceivable for the arrangement grid of the spots to be stretched in one dimension. Alternatively or cumulatively, the buckling lines could also be closed by placing small spots in their path or by at least partially changing the shape of the existing spots so that they extend through the previous buckling lines.

The diaper-fastening tape 103 is complementary with regard to the arrangement of the spots. To this extent, this diaper-fastening tape 103 has only one spot 115A but its edges correspond to the geometry of the diaper-fastening tapes 101, 102 and 105. To this extent, what was said above regarding the arrangement of spots also applies here accordingly because the advantageous arrangement of the edges, edge areas, buckling lines and cut edges is also implemented in this embodiment. The buckling lines in particular are also formed by a suitably weakening in the material, but running through the midpoints of the holes.

The fourth diaper-fastening tape 104 in FIGS. 12 and 13 has a different geometry of the spots in its carrier area 112 than do the four other exemplary embodiments 101, 102, 103, 105. The three spots 119 of the carrier area 112 on the diaper-fastening tape 104 have separate intermediate carriers but the separation occurs only in the direction of the longitudinal extent 107 of the tape 104. Along the machine direction, the spots 119 are strip-shaped and each extends over the entire width of the tape 104. The strip-shaped spots 119 deviate greatly from the rectangular shape in that they have constrictions 140 (labeled with numbers as examples) of the intermediate carrier 120 spaced at regular intervals. The spot edge 124A of the strip-shaped spots 119 within the carrier area 112 is essentially zigzagged-shaped with rounded points over its entire path. At the edge of the carrier area 112 the strip-shaped spots 119 each have a straight edge section 125A which at the same time is over the edge of the diaper-fastening tape 104. The intermediate carriers 120 of the three strip-shaped spots 119 are shaped exactly like the shape of the spots 119 and are completely covered with hooks 122 which are arranged in a very narrow grid pattern aligned with or perpendicular to the direction of the longitudinal extent 107. The shape of the spot edges 124A is thus oblique to the direction of the longitudinal extent 107 not only over the entire path of the edge within the carrier area 112 but also at the same time, in deviation in the regulator arrangement—which here is exclusively parallel or perpendicular to the direction of the longitudinal extent. Since the strip-shaped spots 119 extend to the edge of the carrier area 112, they function at the same time as edge spots with an edge carrier along whose edge sections 125A the border of the carrier area 112 is formed in part.

Between the strip-shaped spots 119, two buckling lines run through the carrier area 112 in a first direction 141. Around these buckling lines, the carrier area can be buckled out of the plane of the tape especially easily. At the same time, due to the lateral weakening 140 in the intermediate carrier 120 which is made of a hard relatively inflexible plastic, this yields the possibility of easily rotating a partial area within the carrier area within the plane of the tape about an axis of rotation perpendicular to the plane of the tape. Therefore, in the effective engagement of the hooks 122 with a corresponding loop component (not shown), an intentional separation of the two components due to mutual rotation in relation to one another is reliably prevented. Even if, in the event of rotation of the components in relation to one another, the edges of the carrier area 112 and its counterpart, which is provided with loops, were to experience a slight separation, the middle area of the carrier area 112 could easily follow the rotation and therefore would become separated.

The same effect is also achieved with the spot geometry according to the exemplary embodiments of the diaper-fastening tapes 101, 102, 103 and 105.

On the whole, the five exemplary embodiments thus illustrate embodiments of the invention in which, according to an important aspect of the present invention, a relative stiff intermediate carrier beneath the mechanical fastener is separated in a targeted manner and additional weakened so that the carrier area presents an excellent compromise between strength and flexibility with the option of flexibly following its counterpart with which it cooperates in the fastening system.

Additional release tapes 150 may be provided between the fastening area 108 and the carrier area 112 on the diaper-fastening tapes 101, 102, 103, 104, 105 or they may also be provided so they extend throughout the carrier area 112. An adhesive layer 151 for securing the release tapes 150 may also be provided on the release tapes 150. In particular, elastic areas 152 may be arranged in the course of the fastening carrier 106 inside or outside the carrier area 112 so that the carrier area 112 can follow the movements of its counterpart even better.

It should also be pointed out that through the proposed means of connection via a closing area 8 with a pop-off securing means and a shear-off securing means in the inventive constellations described here, it is possible to produce a diaper-fastening tape that not only holds very reliably but also can be used in a great variety of ways. For example, it adheres well to an outer membrane on the back sheet (such as that frequently encountered with incontinency diapers, for example) as well as to textile surfaces of a back sheet (such as those usually encountered with baby diapers).

In the plurality of exemplary embodiments shown here and even in the exemplary embodiment illustrated in FIGS. 1 through 5, it is apparent that a target tape and/or a release tape may be provided but need not necessarily be provided to implement an aspect of the invention. If a target is provided, it may be positioned on the back sheet with the first closing of the diaper. It may form a landing zone for the adhesive of the closing area if the diaper is to be opened and closed again and/or a release tape in a traditional manner in the production as a hold-down device for the closing area of the diaper-fastening tape before applying the diaper to the body. To this extent, the target tape and/or the release tape may be omitted. However, it should be pointed out that the constellation of a mechanical closing area and a closing area that is closable by means of an adhesive and a target tape in the closing area and/or a release tape in the closing area, as proposed explicitly here, is inventive by itself.

The invention claimed is:

1. A fastening tape for a hygiene item comprising:
   (a) a fastening area for permanent attachment to the hygiene item;
   (b) a closing area for simultaneous detachable joining to a surface of the hygiene item, said closing area comprising first and second areas, said first area having a shear-off securing component of a two-component mechanical fastening system and said second area having a pop-off securing fastener comprising an adhesive layer;
   (c) a plurality of spot-shaped carriers within a carrier area defined by said spot-shaped carriers, each spot-shaped carrier carrying the shear-off securing component, wherein a selected set of said plurality of spot-shaped carriers comprises a plurality of edge carriers, each edge carrier forming a respective portion of a border of the carrier area along an edge section of the edge carrier, and wherein said set of said plurality of spot-shaped carriers comprises identical strip-shaped spots;
   (d) a fastening carrier fastened to said spot-shaped carriers, said fastening carrier comprising first and second longitudinal portions; and
   (e) a bending line running through the carrier area;
   wherein said adhesive layer comprises at least first and second adhesives extending respectively over the first and second longitudinal portions of the fastening carrier.

2. The fastening tape according to claim 1, wherein the plurality of spot-shaped carriers comprises a plurality of spots having a varying edge in the machine direction and arranged in levels extending in the direction of the longitudinal extent of the fastening tape over the effective width of the carrier area, each level being separated from an adjoining level by a distance in the machine direction, and at least one spot being provided at each level.

3. The fastening tape according to claim 1, wherein the plurality of spot-shaped carriers comprises a plurality of strip-shaped spots formed by a separation in a first direction and by a spaced-apart weakening in a second direction.

4. A strip material having a longitudinal direction of extent which can be divided by separating across the longitudinal direction of extent to form individual usages in the form of fastening tapes according to claim 1.

5. A coil of a strip material according to claim 4.

6. A diaper having a fastening tape according to claim 1.

7. The fastening tape according to claim 3, wherein the plurality of strip-shaped spots comprise at least two strips along the first direction, wherein the strips lie parallel to the first direction and substantially parallel to one another, whereas in the second direction along the profile of the strips, the strips are provided with an edge variation comprising weakenings which are spaced apart from one another, with a constriction of the strips comprising a tapering in the profile so that defined bending lines are obtained in the first direction along the dividing lines of the individual strip-shaped spots and approximately perpendicular hereto, are obtained weaker but nevertheless perceptible further bending lines.

8. A fastening tape for a hygiene item comprising:
   (a) a fastening area for permanent attachment to the hygiene item;
   (b) a closing area for simultaneous detachable joining to a surface of the hygiene item;
   (c) a plurality of spot-shaped carriers within a carrier area defined by said carriers, each spot-shaped carrier carrying a component of a two-component mechanical fastening system, wherein a selected set of said plurality of spot-shaped carriers comprises identical strip-shaped spots;
   (d) a fastening carrier fastened to said spot-shaped carriers, said fastening carrier comprising first and second longitudinal portions; and
   (e) a bending line running through the carrier area;
   wherein when viewed from the fastening area, the closing area initially at least partially comprises hooks and otherwise an open adhesive surface, said open adhesive surface comprising at least first and second adhesives extending respectively over the first and second longitudinal portions of the fastening carrier.

9. The fastening tape according to claim 1, wherein the border of the carrier area near a separation in a machine direction coincides with a longitudinal tape edge.

10. A strip material having a longitudinal direction of extent which can be divided by separating across the longitudinal direction of extent to form individual usages in the form of fastening tapes for a hygiene item, each fastening tape comprising a fastening area for permanent attachment to the hygiene item, a closing area for simultaneous detachable joining to a surface of the hygiene item, a plurality of spot-shaped carriers within a carrier area defined by said spot-shaped carriers, each spot-shaped carrier carrying a component of a two-component mechanical fastening system, a fastening carrier fastened to said spot-shaped carriers, said fastening carrier comprising first and second longitudinal portions, and a bending line running through the carrier area;
   wherein the carrier area has a cohesive open adhesive area between the spot-shaped carriers, said open adhesive area comprising at least first and second adhesives extending respectively over the first and second longitudinal portions of the fastening carrier.

11. The strip material according to claim 10, wherein the strip material is further separated substantially in the longitudinal direction of extent.

* * * * *